(12) United States Patent
Kuehlewind et al.

(10) Patent No.: US 10,401,268 B2
(45) Date of Patent: Sep. 3, 2019

(54) RIG

(71) Applicant: ROLLS-ROYCE plc, London (GB)

(72) Inventors: Rico Kuehlewind, Bristol (GB);
Stephen R Hallett, Bristol (GB); Luiz Kawashita, Bristol (GB)

(73) Assignee: ROLLS-ROYCE plc, London (GB)

( * ) Notice: Subject to any disclaimer, the term of this patent is extended or adjusted under 35 U.S.C. 154(b) by 345 days.

(21) Appl. No.: 15/257,580

(22) Filed: Sep. 6, 2016

(65) Prior Publication Data
US 2017/0089816 A1    Mar. 30, 2017

(30) Foreign Application Priority Data
Sep. 30, 2015 (GB) .................................. 1517240.6

(51) Int. Cl.
*G01N 3/00* (2006.01)
*G01N 3/02* (2006.01)
(Continued)

(52) U.S. Cl.
CPC ................ *G01N 3/02* (2013.01); *B23P 19/04* (2013.01); *G01M 5/0016* (2013.01);
(Continued)

(58) Field of Classification Search
CPC .... G01N 3/02; G01N 3/32; G01N 2203/0023; G01N 2203/0025; G01N 2203/0096;
(Continued)

(56) References Cited

U.S. PATENT DOCUMENTS 2,699,672 A * 1/1955 Couch ..................... G01M 7/08
73/12.13
4,248,096 A * 2/1981 Marcum .................. G01N 3/32
73/828
(Continued)

FOREIGN PATENT DOCUMENTS

CH       702 812 A2    9/2011
CN     101464240 A    6/2009
(Continued)

OTHER PUBLICATIONS

Feb. 3, 2017 Search Report issued in European Patent Application No. 16 18 7400.
(Continued)

*Primary Examiner* — Max H Noori
(74) *Attorney, Agent, or Firm* — Oliff PLC

(57) ABSTRACT

A rig for testing mode II fatigue of a composite component. The rig includes a clamp for clamping one end of the component. A first contact arrangement is provided for contacting one side of the component and a second contact arrangement is provided for contacting an opposing side of the component, the first and second contact arrangements being spaced from the clamp. A loading fork is provided for applying load to the component. The loading fork includes a first and a second portion arranged such that in use, when the loading fork is loading the component in one direction the first portion contacts the first contact arrangement and the second portion is spaced from the second contact arrangement, and when the loading fork is loading the component in an opposite direction the first portion is spaced from the first contact arrangement and the second portion contacts the second contact arrangement.

12 Claims, 6 Drawing Sheets

(51) Int. Cl.
  *G01M 5/00* (2006.01)
  *G01N 3/32* (2006.01)
  *B23P 19/04* (2006.01)
  *G01M 15/14* (2006.01)
(52) U.S. Cl.
  CPC .......... *G01M 5/0033* (2013.01); *G01M 15/14* (2013.01); *G01N 3/32* (2013.01); *G01N 2203/0023* (2013.01); *G01N 2203/0025* (2013.01); *G01N 2203/0096* (2013.01)
(58) Field of Classification Search
  CPC ... B23P 19/04; G01M 5/0016; G01M 5/0033; G01M 15/14
  USPC .......................................................... 73/799
  See application file for complete search history.

(56) References Cited

U.S. PATENT DOCUMENTS

| | | | | |
|---|---|---|---|---|
| 2004/0045162 | A1* | 3/2004 | Beck ..................... | G01N 27/902 29/889.71 |
| 2009/0260451 | A1* | 10/2009 | Li ....................... | G01M 99/005 73/852 |
| 2009/0314100 | A1* | 12/2009 | Myers ..................... | G01N 3/36 73/811 |
| 2013/0081476 | A1* | 4/2013 | Smith ................... | G01M 7/025 73/808 |

FOREIGN PATENT DOCUMENTS

| | | |
|---|---|---|
| WO | 2007/084356 A2 | 7/2007 |
| WO | 2009/112795 A2 | 9/2009 |
| WO | 2011/091081 A1 | 7/2011 |

OTHER PUBLICATIONS

O'Brien et al., "Mode II Interlaminar Fracture Toughness and Fatigue Characterization of a Graphite Epoxy Composite Material," NASA STI Program, 2010.

Matsubara et al., "Mode II fatigue crack growth from delamination in unidirectional tape and satin-woven fabric laminates of high strength GFRP," International Journal of Fatigue, vol. 28, 2006, pp. 1177-1186.

Tanaka et al., "Stress-Ratio Effect on Mode II Propagation of Interlaminar Fatigue Cracks in Graphite/Epoxy Composites," Composite Materials: Fatigue and Fracture (Sixth Volune), 1997, pp. 126-142.

Russell et al., "The Effect of Matrix Toughness on Delmination: Static and Fatigue Fracture Under Mode II Shear Loading of Graphite Fiber Composites," Toughened Composites, 1987, pp. 275-294.

Mar. 15, 2016 Search Report issued in British Patent Application No. 1517240.6.

\* cited by examiner

RIG

TECHNICAL FIELD

The present disclosure concerns a rig and/or a method for testing a composite component in mode II fatigue, and/or a method of manufacture of a composite component and/or a gas turbine engine.

BACKGROUND

Gas turbine engines are typically employed to power aircraft. Typically a gas turbine engine will comprise an axial fan driven by an engine core. The engine core is generally made up of one or more turbines which drive respective compressors via coaxial shafts. The fan is usually driven off an additional lower pressure turbine in the engine core.

The fan comprises an array of radially extending fan blades mounted on a rotor. The fan blades and/or a casing that surrounds the fan may be manufactured from composite laminate materials. Generally composite fan blades include a composite body and may be provided with a metallic leading edge and/or a metallic trailing edge.

Composite components are often laminate structures that include a plurality of plies. Each ply generally includes reinforcing fibres (e.g. high strength and/or high stiffness fibres) embedded in a matrix, e.g. a plastic matrix material. The matrix material of adjacent stacked plies is bonded together to build the composite component. A primary failure mechanism of concern for composite materials is delamination. Delamination for example of a fan blade may occur in the event of an impact by a foreign object such as a bird strike Delamination may occur in mode I failure or mode II failure. As is understood in the art, mode I is inter-laminar cracking where the plies of the laminate peel apart, and mode II is inter-laminar cracking where the plies slide over one another.

Various tests have been devised to determine how a composite laminate component will behave in mode II fatigue failure. To test fatigue failure in a composite component it is necessary to apply reverse loading to the composite component. This has been done using a three point bend test arrangement or by using a cantilever arrangement.

An example of a cantilever arrangement includes incorporating a film in the composite component as a crack initiator and then clamping the component at one end. Load is applied to the opposite end using an arrangement of pins and a plurality of bearings. However, this method of testing includes a complicated loading device and as such the loading is more difficult to control and there is an increased likelihood of failure. Furthermore, the testing equipment can often experience unwanted loads that can affect the fatigue life of the component.

An alternative cantilever arrangement test includes incorporating a film in the composite component as a crack initiator and then clamping the component at one end. A ram is attached to the clamped end to move the end up and down. The opposite end of the component is clamped between two hardened steel rollers that are connected to a load cell. However, in this test method the steel rollers can induce stress concentrations in the component. Furthermore, the component may experience unwanted oscillations and unwanted dynamic affects during a loading cycle that can affect fatigue life of the component.

There is a desire in the industry for an improved rig and method of testing composite components.

SUMMARY

According to a first aspect there is provided a rig for testing mode II fatigue of a composite component. The rig comprises a clamp for clamping one end of the component. The rig further comprises a first contact arrangement for contacting one side of the component and a second contact arrangement for contacting an opposing side of the component, the first and second contact arrangements being spaced from the clamp. The rig further comprises a loading fork for applying load to the component.

The loading fork may comprise a first portion and a second portion arranged such that in use, when the loading fork is loading the component in one direction the first portion contacts the first contact arrangement and the second portion is spaced from the second contact arrangement, and when the loading fork is loading the component in an opposite direction the first portion is spaced from the first contact arrangement and the second portion contacts the second contact arrangement.

The loading fork may comprise a first member and a second member, the first member being arranged to receive one end of the first and/or second contact arrangement and the second member being arranged to receive an opposite end of the first and/or second contact arrangement.

The loading fork may comprise a third member that connects the first and second members.

The loading fork may be connected to a load cell. The loading fork may be connected to a load cell of a servo-hydraulic testing machine. The loading fork may be connected to the load cell via a connecting rod attached (e.g. directly attached) to the third member.

The first member may include a window that defines a first portion and a second portion for contact with the respective contact arrangement. The second member may include a window that defines the first portion and the second portion for contact with the respective contact arrangement.

The window may be shaped and dimensioned so as to permit sliding of the first and/or second contact arrangements in a direction transverse to the loading direction.

The window may be rectangular in shape. The window may include filleted corners.

Each of the first and second contact arrangements may comprise a block member for bonding to the composite component. The block members may be bonded to the composite component using an adhesive.

Each of the first and second contact arrangements may comprise a rod that is received in the block member and is arranged to contact the loading fork.

The block member may include a hole (e.g. a through hole) and the rod may be received in said hole. When the hole is a through hole, the rod may be dimensioned such that both ends of the rod protrude from the block. Alternatively, each block may include a hole on opposing sides, and a rod may be received in each hole.

The rig may include a control system arranged to operate the rig such that the load applied to the component by the loading fork is non-sinusoidal. For example, the load applied may follow a modified sine wave having a linear portion. For example, the loading curve may include a linear portion at ±20% of the maximum load (e.g. the maximum load applied during the test).

An elastomer may be provided in a region between the loading fork and each of the first and second contact arrangements.

The composite component may be an elongate test specimen.

The loading fork may be arranged to apply a load to an end of the composite component opposite the clamp. In use, the test rig may be considered to clamp the composite component in a cantilever arrangement.

According to a second aspect there is provided a method of testing a composite component in mode II fatigue using the rig according to any one of the previous claims. The method comprises clamping the component to the rig using the clamp. The first and second contact arrangements are attached to the composite component at a position spaced from the clamp. The loading fork is moved in a first direction to apply a load to the component in a first direction and the loading fork is moved in a second direction to apply a load to the component in a second direction.

The loading of the component in the first and second direction may be continuously repeated for a given period of time or until a given amount of damage has been sustained by the component.

The method may comprise moving the loading fork such that the load applied to the component is non-sinusoidal.

According to a third aspect there is provided a method of testing a composite component in mode II fatigue. The method comprising clamping one end of the composite component; and loading the composite component at a position spaced from the clamp, wherein the composite component is loaded in one direction by loading one side of the component but leaving the opposing side of the component free from load, and wherein the composite component is loaded in an opposite direction by loading the opposite side of the component but leaving the one side of the component free from load.

According to a fourth aspect there is provided a method of testing a component in mode II fatigue, the method comprising clamping one end of the component and applying a non-sinusoidal reversible load to the component at a position spaced from the position of clamping.

According to a fifth aspect there is provided a method of manufacturing a gas turbine engine that comprises a composite component, the method comprising testing the material used to form the composite component using a method according to the second, third or fourth aspect, and if the material passes the test, assembling of the composite component in the gas turbine engine.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.]— wording used in final draft as part of summary.

DESCRIPTION OF THE DRAWINGS

Embodiments will now be described by way of example only, with reference to the Figures, in which.

DETAILED DESCRIPTION

Figure 1:
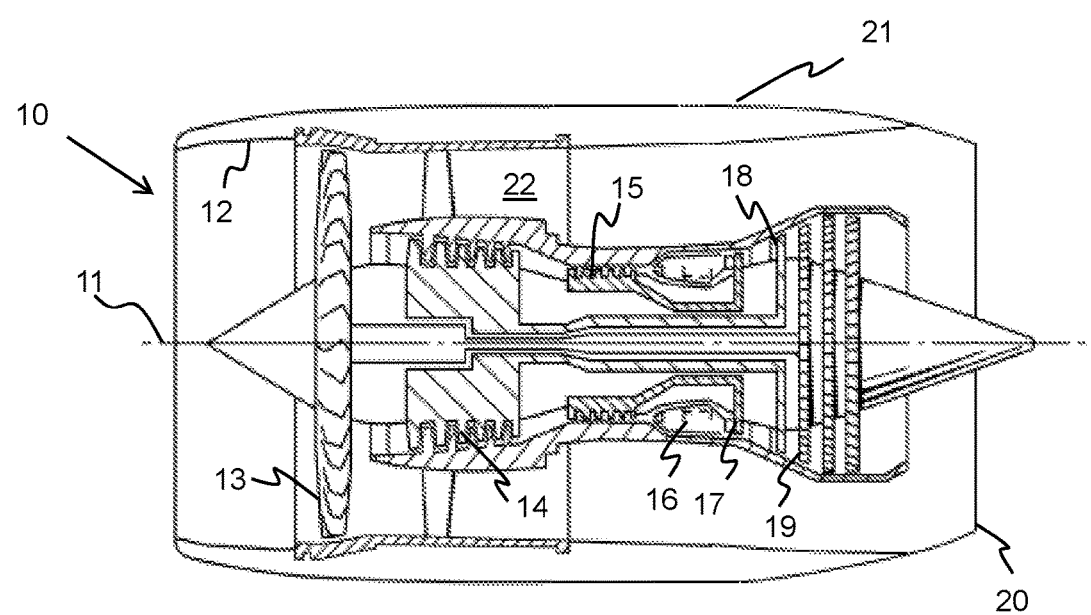
FIG. 1 is a sectional side view of a gas turbine engine.

With reference to FIG. 1, a gas turbine engine is generally indicated at 10, having a principal and rotational axis 11. The engine 10 comprises, in axial flow series, an air intake 12, a propulsive fan 13, an intermediate pressure compressor 14, a high-pressure compressor 15, combustion equipment 16, a high-pressure turbine 17, an intermediate pressure turbine 18, a low-pressure turbine 19 and an exhaust nozzle 20. A nacelle 21 generally surrounds the engine 10 and defines both the intake 12 and the exhaust nozzle 20.

The gas turbine engine 10 works in the conventional manner so that air entering the intake 12 is accelerated by the fan 13 to produce two air flows: a first air flow into the intermediate pressure compressor 14 and a second air flow which passes through a bypass duct 22 to provide propulsive thrust. The intermediate pressure compressor 14 compresses the air flow directed into it before delivering that air to the high pressure compressor 15 where further compression takes place.

The compressed air exhausted from the high-pressure compressor 15 is directed into the combustion equipment 16 where it is mixed with fuel and the mixture combusted. The resultant hot combustion products then expand through, and thereby drive the high, intermediate and low-pressure turbines 17, 18, 19 before being exhausted through the nozzle 20 to provide additional propulsive thrust. The high 17, intermediate 18 and low 19 pressure turbines drive respectively the high pressure compressor 15, intermediate pressure compressor 14 and fan 13, each by suitable interconnecting shaft.

Other gas turbine engines to which the present disclosure may be applied may have alternative configurations. By way of example such engines may have an alternative number of interconnecting shafts (e.g. two) and/or an alternative number of compressors and/or turbines. Further the engine may comprise a gearbox provided in the drive train from a turbine to a compressor and/or fan.

The fan 13 includes a plurality of fan blades arranged around a hub. A fan casing circumscribes the fan. In exemplary embodiments the fan casing and/or the fan blades may be made at least in part from a composite material, such as carbon fibre in a resin matrix.

A rig for and a method of testing a composite material that can be used to form at least part of the casing and/or fan blade will now be described.

Figure 2:
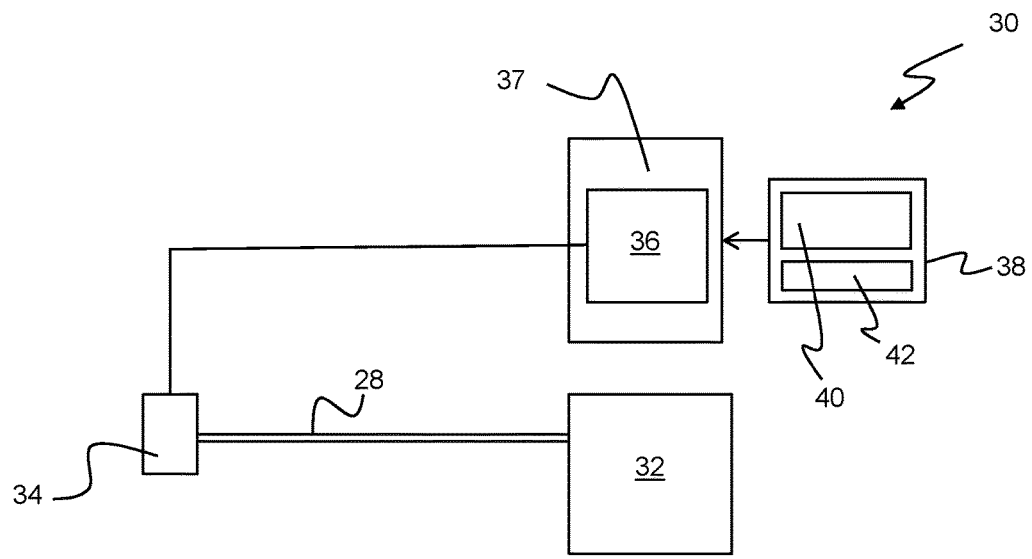
FIG. 2 is a schematic of a rig for use in testing mode II fatigue of a composite component.

Referring now to FIG. 2, a rig for testing a composite component 28 is indicated generally at 30. In this example the composite component is an elongate specimen that has a rectangular and substantially constant cross section. The rig includes a clamp 32 for clamping one end of the composite component. The rig further includes a loading fork 34 for applying a reversible load to the component at a position spaced from the clamp 32, and in this example at an opposite end of the component to the end that is clamped.

The loading fork 34 is connected to a load cell 36. In this example the loading fork is directly connected to the load cell, i.e. without the use of hydraulic grips for example. The load cell in this example is a load cell of a servo-hydraulic testing machine 37 that communicates with a control unit 38. The testing machine and control unit may be considered a control system for controlling the load applied during a test.

The control unit 38 may comprise any suitable circuitry to cause performance of the methods described herein. The control unit may comprise: at least one application specific integrated circuit (ASIC); and/or at least one field programmable gate array (FPGA); and/or single or multi-processor architectures; and/or sequential (Von Neumann)/parallel architectures; and/or at least one programmable logic controllers (PLCs); and/or at least one microprocessor; and/or at least one microcontroller, to perform the methods.

By way of an example, the control unit 38 may comprise at least one processor 40 and at least one memory 42. The memory 42 may store a computer program comprising computer readable instructions that, when read by the processor 40, causes performance of the methods described herein. The computer program may be software or firmware, or may be a combination of software and firmware.

In one example, the computer program may include a user inputted routine that controls displacement of the loading fork 34.

The processor 40 may include at least one microprocessor and may comprise a single core processor, or may comprise multiple processor cores (such as a dual core processor or a quad core processor).

The memory 42 may be any suitable non-transitory computer readable storage medium, data storage device or devices, and may comprise a hard disk and/or solid state memory (such as flash memory). The memory 42 may be permanent non-removable memory, or may be removable memory (such as a universal serial bus (USB) flash drive).

The control system may be provided separately to the test rig or integrally with the test rig. The control system in this example operates in an open loop, but in alternative embodiments the control system may operate in a closed loop.

Figure 3:
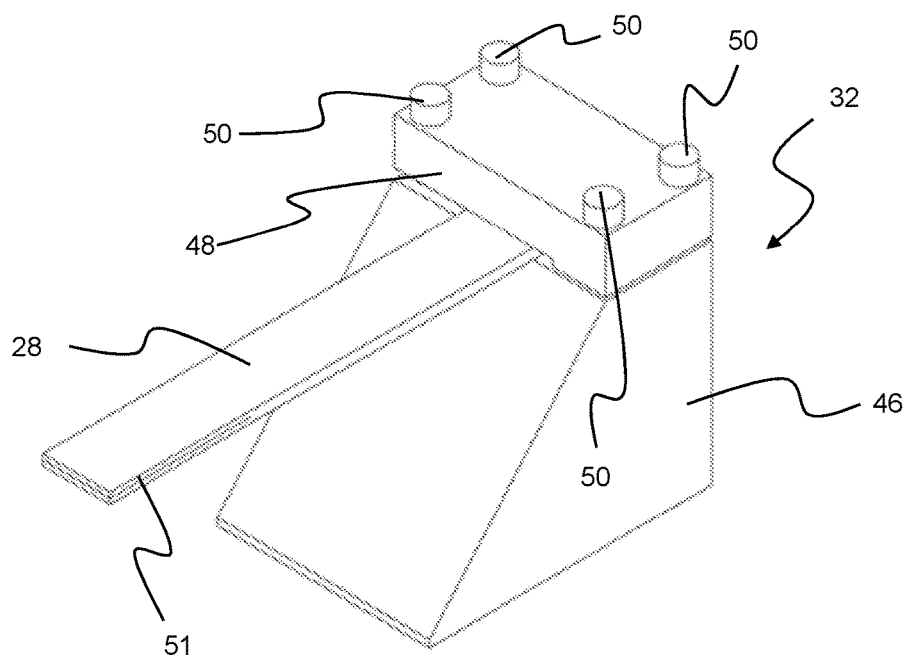
FIG. 3 is a perspective view of a clamp of the rig of FIG. 2 clamping a composite component.

Referring now to FIG. 3, the clamp 32 includes a base member 46 and a top member 48. The component 28 is clamped between the base member and the top member, in this example screws 50 are used to fixedly secure the top member to the base member and to restrict movement of one end of the component. In the present example the clamp is made from steel, but any suitable material may be used.

The component 28 includes a film 51 that simulates a crack that has initiated between the layers of the composite component.

Figure 4:
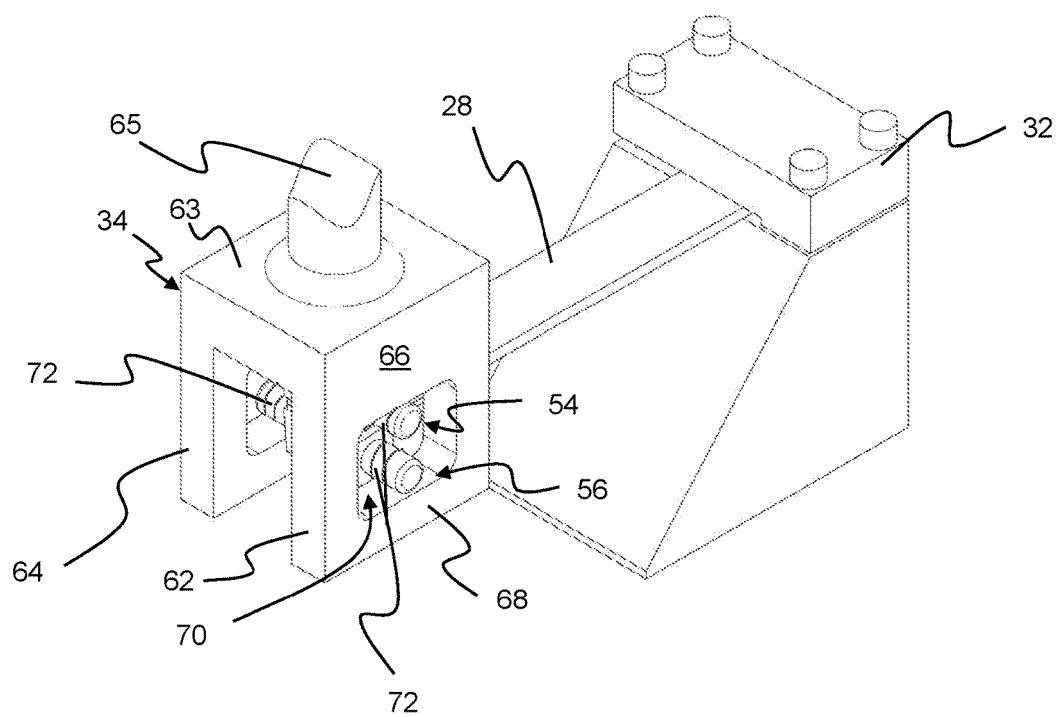
FIG. 4 is a perspective view of the clamp and composite component, a loading fork, and contact arrangements of the rig of FIG. 2.

Referring now to FIG. 4, the loading fork 34 is provided in this example at an opposite end of the component to the clamp 32. The rig also includes a first contact arrangement 54 and second contact arrangement 56 that are connected to the component 28 and via which the loading fork applies load to the component.

Figure 5:
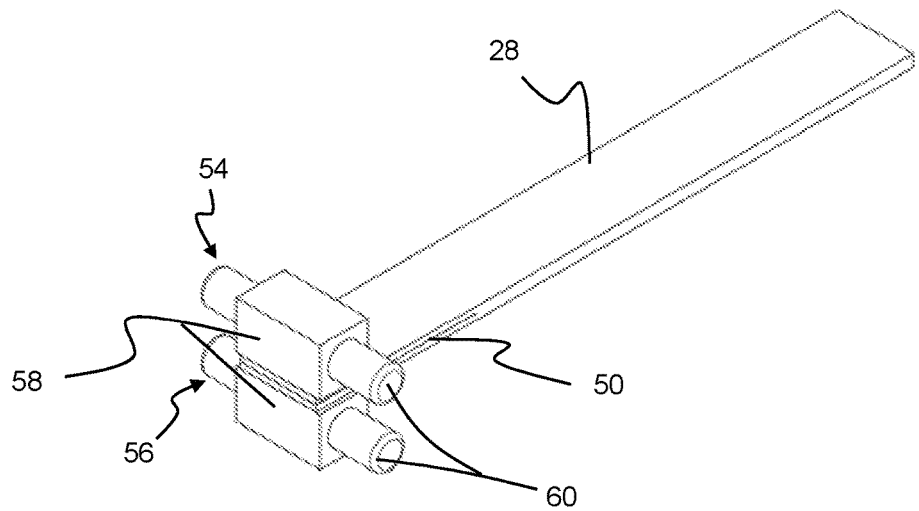
FIG. 5 is a perspective view of the composite component and contact arrangements of FIG. 4.

Referring now to FIG. 5, the first contact arrangement 54 and the second contact arrangement 56 each include a block 58 and a rod 60. Each block 58 is bonded to one of a pair of opposing sides of the component (in this example, one block is bonded to an upper surface of the composite component and one block is bonded to an under surface of the composite component). The blocks may be bonded using for example an adhesive. The blocks each include a hole extending through the width of the block, and one of the rods is inserted in each hole. The rods are dimensioned so as to protrude at each end from the block.

An elastomer ring 72 is placed around the ends of the rods. In this example the rods are circular in cross section.

Referring now to FIGS. 4 and 6 to 8, the loading fork 34 includes a first member 62 for contacting one end of the rods 60 and a second member 64 for contacting the other end of the rods 60. The elastomer ring 72 is positioned so as be an intermediate member between the rod and the loading fork during loading. A third member 63 extends between the first and second member. In the present example, the first, second and third members are integrally formed. The loading fork is connected to a rod 65 at the third member and the rod extends to the load cell 36.

The first and second members each include a first portion 66 and a second portion 68, the first portion being arranged to contact the rod of the first contact arrangement during loading in one direction and the second portion being arranged to contact the rod of the second contact arrangement during loading in the opposite direction. In the present example the first and second portions are defined by a window (or cut-out) 70 provided in each of the first and second members. The window is rectangular in shape and includes filleted corners.

Figure 6:
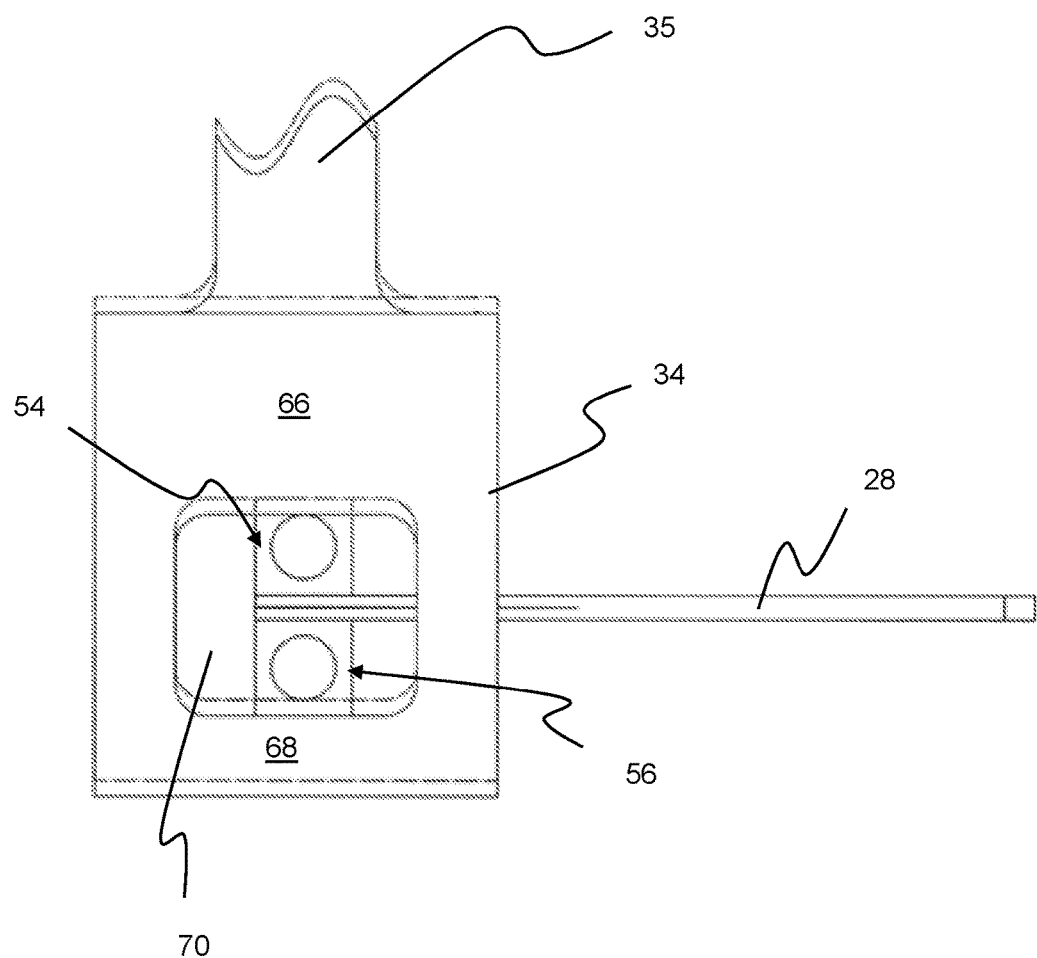
FIG. 6 is a side view of the composite component, loading fork and contacting arrangements of FIG. 4, the dotted outline indicates the relative position of the contact arrangements and loading fork when the loading fork is moving upwards and the solid line indicates the relative position of the contact arrangements and loading fork when the loading fork is moving downwards.
Figure 7:
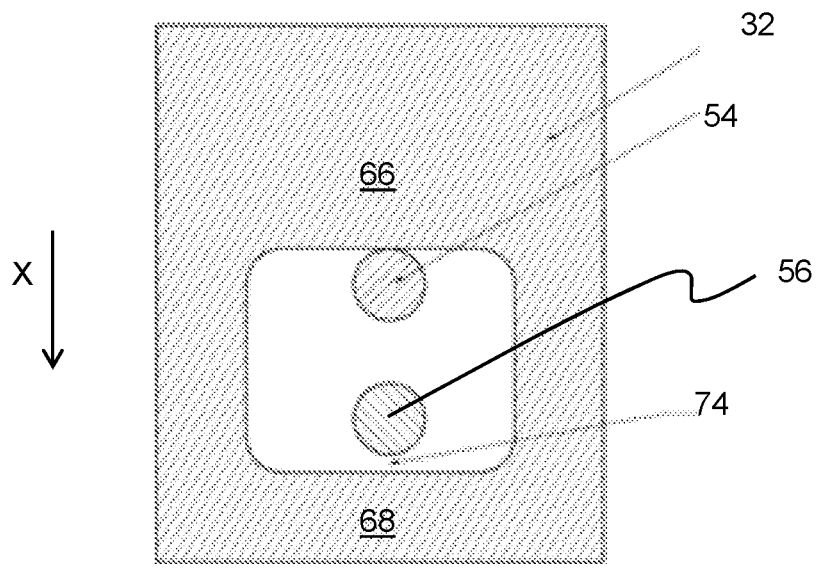
FIG. 7 is a schematic side view of the loading fork and rods of the contacting arrangements of FIG. 6 when the loading fork is moving downwards.
Figure 8:
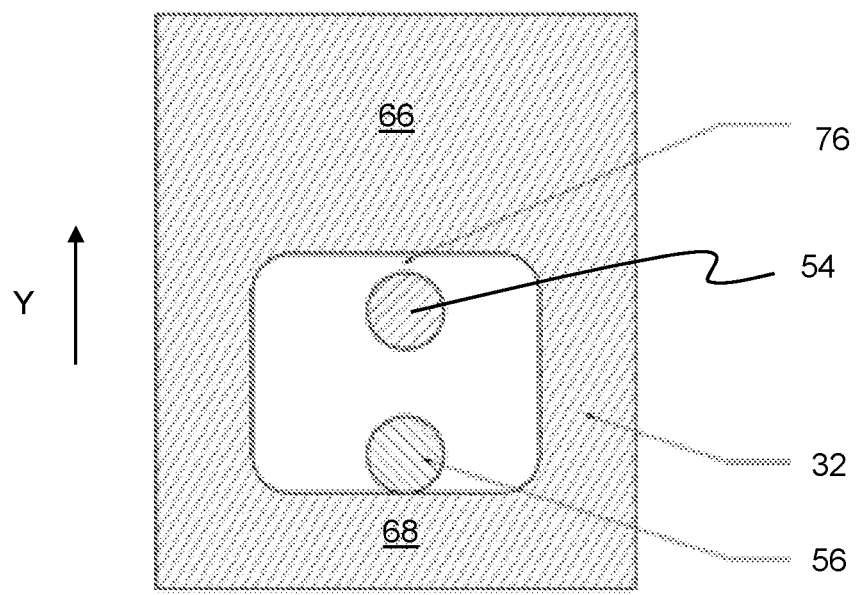
FIG. 8 is a schematic side view of the loading fork and rods of the contacting arrangements of FIG. 8 when the loading fork is moving upwards.

The window 70 is dimensioned such that the loading fork 32 contacts only one of the first or second contact arrangements 66, 68 at any one time. As can be seen in FIGS. 6 to 8, when the loading fork is moving in a first direction X, in this example downwards, the first portion of the loading fork contacts the rod of the first contact arrangement and the rod of the second contact arrangement is spaced by a distance 74 from the second portion. When the direction of loading is reversed to an opposing direction Y, in this example upwards, the second portion contacts the rod of the second contact arrangement and the first portion is spaced from the rod of the first contact arrangement by a distance 76.

The window 70 is also dimensioned so as to be wider than the diameter of the rods of the contact arrangement. In this way sliding of the rods in a direction transverse to the direction of loading is permitted.

To test a component 28, first the elongate test specimen is manufactured and includes the film 51. The specimen is manufactured to represent the material of the final component, for example the material of a fan blade or a casing of a gas turbine engine. However, in alternative embodiments full or partial components may be tested, for example the rig could be modified to receive a fan blade for testing.

Next, one of the blocks 58 of the contact arrangements is bonded to one face of the component (e.g. an upper face of the component) and the other of the blocks of the contact arrangements is bonded to the opposing face of the component (e.g. an under face of the component).

An end of the component opposite the blocks 58 is then positioned in the clamp 32 and the screws 50 are tightened to securely fix the component in the clamp. Once the component is clamped in position the rods 60 are inserted into the holes of the blocks 58 and through the window 70 of the loading fork 32.

Testing is commenced by moving the loading fork 32 in opposing directions, up and down in this case. As shown in FIG. 7, when the loading fork is moving downwards the loading fork 32 contacts the rod of the first contact arrangement 54 and there is no contact between the rod of the second contact arrangement 56 and the loading fork. As shown in FIG. 8, when the loading fork is moving upwards the loading fork 32 contacts the rod of the second contact arrangement 56 and there is no contact between the rod of the first contact arrangement 54 and the loading fork. The cycles of loading are repeated as many times as required for a given test.

To reduce potential impact loads on the component 28, the displacement 'curve' of the loading fork is actively controlled during each load cycle, using the servo hydraulic test machine 37 (e.g. by varying the crosshead displacement curve). In cyclic loading arrangements of the prior art, a simple sinusoidal displacement curve is used. A sinusoidal displacement curve will have the steepest slope (hence maximum velocity) when the loading direction changes. This could result in unwanted impact loads on the component. Further, in the described rig, there will be a small clearance between both the rods and the loading fork for a short period of time whenever the fork passes through the 'zero' displacement point. This could also contribute to unwanted impact loads on the component. To account for this, the servo-hydraulic testing machine is programmed so that the displacement curve is no longer sinusoidal, but has a modified slope when the load direction changes to reduce the impact speed on the specimen.

Figure 9:
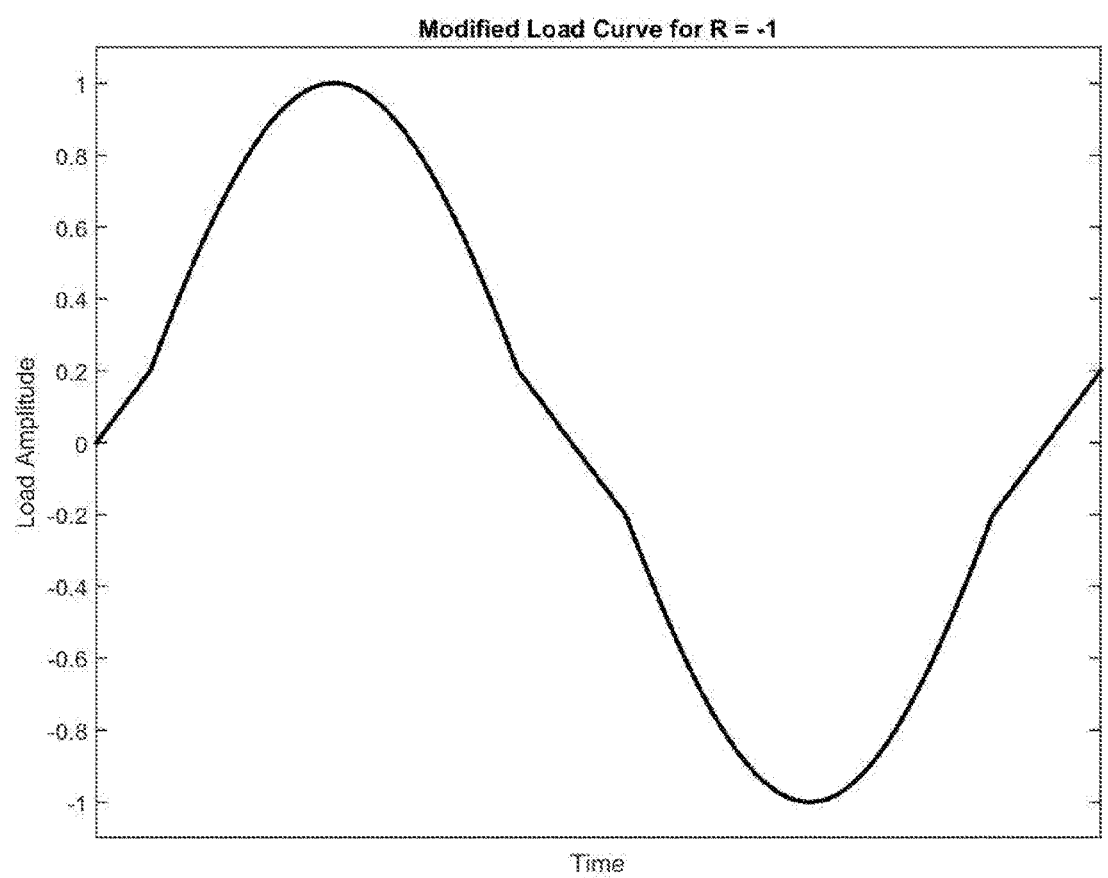
FIG. 9 is a plot of load against time, the load is normalised against the maximum and minimum load (with 1 and −1 being the peak loads).

An example of a portion of the loading curve for a fatigue test is shown in FIG. 9. The loading curve of FIG. 9 is generally a sinusoidal load curve modified such that when the load where at the range between plus or minus 20% of the maximum load capacity the sinusoidal function is replaced with a linear function of the same monotonicity as the previous sinusoidal part of the function. The sign of the gradient corresponds to the sign of the gradient of the sinusoidal function.

Before fully reversed fatigue testing, a test specimen is used to perform a compliance calibration. Based on the calibration, the change in compliance during the test indicates crack growth. Additionally or alternatively, the crack growth may be monitored with a camera that takes a picture after a given cycle count. From these pictures the crack growth can be monitored.

Using the described arrangement means that a load is only ever applied at the loaded end to the component in one direction, because one of the rods does not contact the component. This reduces the risk of the component being pulled open and loading that is not in mode II being applied to the component. As such, the results from the test are improve compared to methods of the prior art.

The width of the window 70 means that the rods can slide within the window when the component is bent without imparting horizontal loading (other than friction) on the component. This means that there is no need for a "sled" or linear bearing, as is needed with some rigs of the prior art, and as such the rig arrangement is simplified.

The elastomer rings provided on the ends of the rods further dampen any impact loads and therefore reduce unwanted specimen oscillation.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. A method of testing a composite component in mode II fatigue using a rig comprising:
   a clamp for clamping one end of the component;
   a first contact arrangement for contacting one side of the component and a second contact arrangement for contacting an opposing side of the component, the first and second contact arrangements being spaced from the clamp; and
   a loading fork for applying load to the component; wherein the loading fork comprises a first portion and a second portion arranged such that in use, when the loading fork is loading the component in one direction the first portion contacts the first contact arrangement and the second portion is spaced from the second contact arrangement, and when the loading fork is loading the component in an opposite direction the first portion is spaced from the first contact arrangement and the second portion contacts the second contact arrangement, the method comprising:
   clamping the component to the rig using the clamp;
   attaching the first and second contact arrangements to the composite component at a position spaced from the clamp;
   moving the loading fork in a first direction apply a load to the component in a first direction and moving the loading fork in a second direction to apply a load to the component in a second direction.

2. The method according to claim 1, wherein the method comprises moving the loading fork such that the load applied to the component is non-sinusoidal.

3. A method of testing a composite component in mode II fatigue, the method comprising:
   clamping one end of the composite component;
   loading the composite component at a position spaced from the clamp, wherein the composite component is loaded in one direction by loading one side of the component but leaving the opposing side of the component free from load, and wherein the composite component is loaded in an opposite direction by loading the opposite side of the component but leaving the one side of the component free from load.

4. A method of manufacturing a gas turbine engine that comprises a composite component, the method comprising:
   testing the material used form the composite component using a method according to claim 1, and
   if the material passes the test, assembling of the composite component in the gas turbine engine.

5. A rig for testing mode II fatigue of a composite component, the rig comprising:
   a clamp for clamping one end of the component;
   a first contact arrangement for contacting one side of the component and a second contact arrangement for contacting an opposing side of the component, the first and second contact arrangements being spaced from the clamp; and
   a loading fork for applying load to the component;
   wherein the loading fork comprises a first portion and a second portion arranged such that in use, when the loading fork is loading the component in one direction the first portion contacts the first contact arrangement and the second portion is spaced from the second contact arrangement, and when the loading fork is loading the component in an opposite direction the first portion is spaced from the first contact arrangement and the second portion contacts the second contact arrangement.

6. The rig according to claim 5, wherein the loading fork comprises a first member and a second member, the first member being arranged to receive one end of the first and/or second contact arrangement and the second member being arranged to receive an opposite end of the first and/or second contact arrangement.

7. The rig according to claim 6, wherein the first member includes a window that defines the first portion and the second portion for contact with the respective contact arrangement, and wherein the second member includes a window that defines the first portion and the second portion for contact with the respective contact arrangement.

8. The rig according to claim 7, wherein the window is shaped and dimensioned so as to permit sliding of the first and/or second contact arrangements in a direction transverse to the loading direction.

9. The rig according to claim 5, wherein each of the first and second contact arrangements comprises a block member for bonding to the composite component.

10. The rig according to claim 9, wherein each of the first and second contact arrangements comprises a rod that is received in the block member and is arranged to contact the loading fork.

11. The rig according to claim 5, wherein the rig includes a control system arranged to operate the rig such that the load applied to the component by the loading fork is non-sinusoidal.

12. The rig according to claim 5, wherein an elastomer is provided in a region between the loading fork and each of the first and second contact arrangements.

* * * * *